(12) United States Patent  (10) Patent No.: US 8,938,113 B2
Kovalan et al.  (45) Date of Patent: Jan. 20, 2015

(54) ADAPTIVE VISUALIZATION FOR DIRECT PHYSICIAN USE

(75) Inventors: Kovey Kovalan, Stamford, CT (US); Nickolay Brailko, San Marcos, CA (US)

(73) Assignee: Kjaya, LLC, Stamford, CT (US)

( * ) Notice: Subject to any disclaimer, the term of this patent is extended or adjusted under 35 U.S.C. 154(b) by 165 days.

(21) Appl. No.: 13/811,559

(22) PCT Filed: Jul. 22, 2011

(86) PCT No.: PCT/US2011/045047
§ 371 (c)(1),
(2), (4) Date: Jan. 22, 2013

(87) PCT Pub. No.: WO2012/018560
PCT Pub. Date: Feb. 9, 2012

(65) Prior Publication Data
US 2013/0121548 A1  May 16, 2013

Related U.S. Application Data

(60) Provisional application No. 61/367,610, filed on Jul. 26, 2010.

(51) Int. Cl.
| | |
|---|---|
| *G06K 9/00* | (2006.01) |
| *G06T 7/00* | (2006.01) |
| *G06T 15/08* | (2011.01) |
| *G06N 3/08* | (2006.01) |
| *A61B 5/055* | (2006.01) |

(Continued)

(52) U.S. Cl.
CPC ............. *G06T 7/0014* (2013.01); *G06T 15/08* (2013.01); *G06T 7/0081* (2013.01); *G06N 3/086* (2013.01); *A61B 5/055* (2013.01); *A61B 6/032* (2013.01); *A61B 6/466* (2013.01); *G06T 2207/20084* (2013.01); *G06T 2207/30004* (2013.01)
USPC ............................................... 382/131; 378/4

(58) Field of Classification Search
USPC ................. 382/100, 128, 129, 130, 131, 132; 128/922; 378/4–27
See application file for complete search history.

(56) References Cited

U.S. PATENT DOCUMENTS

| | | | | |
|---|---|---|---|---|
| 5,631,974 | A * | 5/1997 | Lau-Kee et al. | 382/132 |
| 6,937,767 | B1 * | 8/2005 | Burak et al. | 382/232 |
| 6,950,494 | B2 * | 9/2005 | Vija et al. | 378/62 |

(Continued)

*Primary Examiner* — Anand Bhatnagar
(74) *Attorney, Agent, or Firm* — DeLio, Peterson & Curcio, LLC; Peter W. Peterson

(57) ABSTRACT

A method of modifying a three dimensional (3D) volume visualization image of an anatomical structure in real time to separate desired portions thereof. The method includes providing a two dimensional (2D) image slice of a 3D volume visualization image of an anatomical structure, identifying portions of the anatomical structure of interest, and providing a prototype image of desired portions of the anatomical structure. The method then includes using an evolver to evolve parameters of an algorithm that employs a transfer function to map optical properties to intensity values coinciding with the portions of the anatomical structure of interest to generate an image that sufficiently matches the prototype image. If the parameters match the prototype image, the method then includes applying the transfer function to additional 2D image slices of the 3D volume visualization image to generate a modified 3D volume visualization image of the anatomical structure. The method includes using a pattern recognizer to assist the evolver, to classify whether a view is normal or abnormal, and to extract the characteristic of an abnormality if and when detected.

62 Claims, 10 Drawing Sheets

(51) Int. Cl.
*A61B 6/03* (2006.01)
*A61B 6/00* (2006.01)

(56) References Cited

U.S. PATENT DOCUMENTS 7,190,836 B2 3/2007 Krishnan
2004/0175034 A1 9/2004 Wiemker et al.
2007/0127791 A1* 6/2007 Ernvik et al. .................. 382/128
2007/0232867 A1* 10/2007 Hansmann .................... 600/300
2007/0276214 A1* 11/2007 Dachille et al. ............... 600/407
2008/0317308 A1* 12/2008 Wu et al. ....................... 382/128
2012/0098838 A1* 4/2012 Lehmann et al. ............. 345/501
2013/0004039 A1* 1/2013 Masumoto .................... 382/128

* cited by examiner

ADAPTIVE VISUALIZATION FOR DIRECT PHYSICIAN USE

TECHNICAL FIELD

The present invention relates to computer processing of three dimensional medical images and, in particular, to a method and system for modifying a three dimensional (3D) volume visualization image of an anatomical structure in real time to delineate desired portions thereof.

BACKGROUND ART

A visual medical scan such as computed tomography (CT) or magnetic resonance imaging (MRI) is acquired thru cross sections (FIG. 1A), for example CT scan has an axial cross sections acquisition. Sagittal 10, Coronal 12 and Oblique 14 sections and 3D visualizations may be generated automatically and on demand. However, the automatic 3D image may have the rib cage blocking the heart from being visible (FIG. 1B). A segmentation task would involve removing the bone from this view. According to standard practice, segmentations are prepared by scanner technologist and saved as snapshots for radiologists to view and use for diagnosis (FIG. 1D). For instance, these series of images may include images of coronal maximum intensity projection (MIP) multiplanar reconstruction (MPR) 20, oblique sagittal carotid bifurcation MIP MPR 21, coronal/sagittal arch MIP MPR 22, volume rendered 23, MIP 24 and curved reformats vertebral and through carotid siphons 25.

Research and development of medical image segmentation has illustrated computer vision solutions using digital image processing techniques. The current techniques emanate from having to improve scan technicians' ability from having to sketch the contours slice by slice using pointing devices such as a mouse or trackball, which they note that this is a very time-consuming and the results may suffer from intra-observer or inter-observer variability. Researchers have been focused on developing algorithms to improve computer aided segmentation conducted by technicians, by incorporating modern mathematical and physical techniques on image appearance as well as information from imaging devices and physician's professional knowledge, to greatly enhance the accuracy of segmentation results. The techniques can be categorized as thresholds, clustering, and deformable model based. These segmentation techniques are both computer and human intensive that a lab technician is given the responsibility to pre-segment a scan. This may exclude subtle but crucial information needed for an early diagnosis of a disease. Also, due to the time and cost aspects, segmentation has become an exception rather than an intrinsic part of a diagnosis workflow. Moreover, medical scan size is becoming larger and therefore diagnostic interpretation is becoming harder, and the need for segmentation is becoming more critical. Segmentation becomes an intrinsic part of diagnosis workflow in the method and system of the present invention.

A genetic algorithm (GA) is a search heuristic that mimics the process of natural evolution. This heuristic is routinely used to generate useful solutions to optimization and search problems. Genetic algorithms belong to the larger class of evolutionary algorithms (EA), which generate solutions to optimization problems using techniques inspired by natural evolution, such as inheritance, mutation, selection, and crossover.

In a genetic algorithm, a population of strings (called chromosomes or the genotype of the genome, and also referred to as a "gene"), which encode candidate solutions (called individuals, creatures, or phenotypes) to an optimization problem, evolves toward better solutions. Traditionally, solutions are represented in binary as strings of 0s and 1s, but other encodings are also possible. The evolution usually starts from a population of randomly generated individuals and happens in generations. In each generation, the fitness of every individual in the population is evaluated, multiple individuals are stochastically selected from the current population (based on their fitness), and modified (recombined and possibly randomly mutated) to form a new population. The new population is then used in the next iteration of the algorithm. Commonly, the algorithm terminates when either a maximum number of generations has been produced, or a satisfactory fitness level has been reached for the population. If the algorithm has terminated due to a maximum number of generations, a satisfactory solution may or may not have been reached.

A typical genetic algorithm requires a genetic representation of the solution domain and a fitness function to evaluate the solution domain. A standard representation of the solution is as an array of bits. Arrays of other types and structures can be used in essentially the same way. The main property that makes these genetic representations convenient is that their parts are easily aligned due to their fixed size, which facilitates simple crossover operations. Variable length representations may also be used, but crossover implementation is more complex in this case. Tree-like representations are explored in genetic programming and graph-form representations are explored in evolutionary programming.

The fitness function is defined over the genetic representation and measures the quality of the represented solution. The fitness function is always problem dependent. For instance, in the knapsack problem one wants to maximize the total value of objects that can be put in a knapsack of some fixed capacity. A representation of a solution might be an array of bits, where each bit represents a different object, and the value of the bit (0 or 1) represents whether or not the object is in the knapsack. Not every such representation is valid, as the size of objects may exceed the capacity of the knapsack. The fitness of the solution is the sum of values of all objects in the knapsack if the representation is valid, or 0 otherwise. If it is difficult to define the fitness expression, then interactive genetic algorithms may be used.

Once the genetic representation and the fitness function are defined, GA proceeds to initialize a population of solutions randomly, then improve it through repetitive application of mutation, crossover, inversion and selection operators. Initially many individual solutions are randomly generated to form an initial population. The population size depends on the nature of the problem, but typically contains several hundreds or thousands of possible solutions. Traditionally, the population is generated randomly, covering the entire range of possible solutions (the search space). Occasionally, the solutions may be "seeded" in areas where optimal solutions are likely to be found.

During each successive generation, a proportion of the existing population is selected to breed a new generation. Individual solutions are selected through a fitness-based process, where fitter solutions (as measured by a fitness function) are typically more likely to be selected. Certain selection methods rate the fitness of each solution and preferentially select the best solutions. Other methods rate only a random sample of the population, as this process may be very time-consuming.

The next step is to generate a second generation population of solutions from those selected through genetic operators: crossover (also called recombination), and/or mutation. For each new solution to be produced, a pair of "parent" solutions is selected for breeding from the pool selected previously. By producing a "child" solution using the above methods of crossover and mutation, a new solution is created which typically shares many of the characteristics of its "parents." New parents are selected for each new child, and the process continues until a new population of solutions of appropriate size is generated. Although reproduction methods that are based on the use of two parents are more "biology inspired," some research suggests more than two "parents" are better to be used to reproduce a good quality chromosome.

These processes ultimately result in the next generation population of chromosomes that is different from the initial generation. Generally the average fitness will have increased by this procedure for the population, since only the best organisms from the first generation are selected for breeding, along with a small proportion of less fit solutions, for reasons already mentioned above. Although Crossover and Mutation are known as the main genetic operators, it is possible to use other operators such as regrouping, colonization-extinction, or migration in genetic algorithms This generational process is repeated until a termination condition has been reached. Common terminating conditions are: 1) a solution is found that satisfies minimum criteria; 2) fixed number of generations reached; 3) allocated budget (computation time/money) reached; 4) the highest ranking solution's fitness is reaching or has reached a plateau such that successive iterations no longer produce better results; 5) manual inspection; and/or 6) combinations of the above.

The simple generational genetic algorithm procedure involves the following steps: 1) choose the initial population of individuals; 2) evaluate the fitness of each individual in that population; 3) repeat on this generation until termination (time limit, sufficient fitness achieved, etc.) as follows: a) select the best-fit individuals for reproduction; b) breed new individuals through crossover and mutation operations to give birth to offspring; c) evaluate the individual fitness of new individuals; d) replace least-fit population with new individuals.

A neural network (NN) is a mathematical model or computational model that is inspired by the structure and/or functional aspects of biological neural networks. A neural network consists of an interconnected group of artificial neurons, and it processes information using a connectionist approach to computation. In most cases an NN is an adaptive system that changes its structure based on external or internal information that flows through the network during the learning phase. Modern neural networks are non-linear statistical data modeling tools. For NN to be useful in providing solution to a difficult problem, the network has to be first trained using exemplarily data from the domain of the problem. NN are usually used to model complex relationships between inputs and outputs or to find patterns in data.

Convolution NN is a type of NN and is well suited for image recognition tasks such as for fingerprint identification or facial recognition.

DISCLOSURE OF INVENTION

Bearing in mind the problems and deficiencies of the prior art, it is therefore an object of the present invention to provide an improved method of modifying a three dimensional volume visualization image of an anatomical structure in real time.

It is another object of the present invention to provide a method that enables physicians to control views generated from a three dimensional image of an anatomical structure in real time during diagnosis instead of relying on scan technologists to generate those views.

A further object of the invention is to provide a method to assist physicians in making accurate diagnostic decisions using segmented views.

It is yet another object of the present invention to provide a set of methods serving as a foundation for future research and outcome to assist physician in making accurate diagnostic decisions.

Still other objects and advantages of the invention will in part be obvious and will in part be apparent from the specification.

The above and other objects, which will be apparent to those skilled in the art, are achieved in the present invention which is directed in one aspect to a method of modifying a three dimensional (3D) volume visualization image of an anatomical structure in real time to separate desired portions thereof comprising providing a two dimensional (2D) image slice of a 3D volume visualization image of an anatomical structure, identifying portions of the anatomical structure of interest, and providing a prototype image of desired portions of the anatomical structure. The method then includes using an evolver to evolve parameters of an algorithm that employs a transfer function to map optical properties to intensity values coinciding with the portions of the anatomical structure of interest to generate an image that sufficiently matches the prototype image. If the parameters match the prototype image, the method then includes applying the transfer function to additional 2D image slices of the 3D volume visualization image to generate a modified 3D volume visualization image of the anatomical structure.

The optical properties may comprise color and/or transparency values. The evolver may be a genetic algorithm. The parameter values define a set of graphical elements selecting a histogram. The algorithm employs graphical elements selecting a histogram to generate a transfer function.

A pattern recognizer may be used to determine a fitness function of the genetic algorithm by evaluating whether the transfer function generated image sufficiently matches the prototype image, and the method may include assigning a fitness value between 0.0 and 1.0 reflecting the degree at which the images match. The pattern recognizer can be a neural network model. The neural network model may be previously trained to recognize analogous images. The neural network model may be used to determine whether the transfer function generated image matches the prototype image, the neural network being adapted to recognize visual patterns directly from pixel images of the transfer function generated image and the prototype image. The neural network model may be used to classify whether a view is normal or abnormal and the characteristic of an abnormality extracted from the neural network model. The neural network may employ a convolution neural network model.

Alternatively, a root mean squared error (Ei) fitness function may be used to determine whether the transfer function generated image sufficiently matches the prototype image, and the method includes assigning a fitness value between 0.0 and 1.0 reflecting the degree at which the images match.

The method may further include, if the transfer function generated image does not sufficiently match the prototype image, then continuing to evolve the parameters of the algorithm, and repeating the aforementioned steps. The method may also include using the matched genotype or transfer function in future modifications of a 3D volume visualization image of an anatomical structure to separate desired portions thereof, using the aforementioned steps. The matched genotype or transfer function may be used to generate views in lieu of scan technologist segmentation protocols.

In another aspect the present invention is directed to a method of displaying adaptive visualization on a remote client application and a three dimensional (3D) volume visualization image at centralized server application thereof comprising providing a two dimensional (2D) image slice of a 3D volume visualization image of an anatomical structure, identifying a view of interest on the remote client application, and transmitting view of interest information to the centralized server application. The method then includes using an evolver to evolve transfer-function-parameters of an algorithm that maps optical properties to intensity values to produce a view of interest in the form of a rendered image. The method further includes using an evolver to evolve compression-parameters of an algorithm that optimizes the compression algorithm to compress the rendered image, and then using an evolver to evolve transmission-parameters of an algorithm that optimizes the transmission of the compressed image from the centralized server to the remote client application.

The optimization of compression-parameters may produce the highest compression ratio while maintaining diagnostic quality, and the optimization of transmission-parameters may produce the fastest transmission to the remote client application.

A pattern recognizer may be used to determine whether the view is flagged as normal or abnormal by the centralized server application, and the neural network model may be previously trained to recognize normal or abnormal views. The pattern recognizer can be a neural network model.

The method may include sending a flag or warning to the remote client application to alert a user as to whether the view is normal or abnormal, with or without also identifying and sending the abnormal section of the view to the remote client application to alert the user. The user may be a radiologist or a physician.

The evolver may be a genetic algorithm. The parameter values define a set of graphical elements selecting a histogram. The algorithm employs graphical elements selecting a histogram to generate a transfer function.

A pattern recognizer may be used to determine a fitness function of the genetic algorithm by evaluating whether the rendered image sufficiently matches the prototype image, and the method may include assigning a fitness value between 0.0 and 1.0 reflecting the degree at which the images match. The pattern recognizer can be a neural network model. The neural network model may be previously trained to recognize analogous images. The neural network model may be used to determine whether the rendered image matches the prototype image, the neural network being adapted to recognize visual patterns directly from pixel images of the rendered image and the prototype image. The neural network model may be used to classify whether a view is normal or abnormal and the characteristic of an abnormality extracted from the neural network model. The neural network may employ a convolution neural network model.

Alternatively, a root mean squared error (Ei) fitness function may be used to determine whether the rendered image sufficiently matches the prototype image, and the method includes assigning a fitness value between 0.0 and 1.0 reflecting the degree at which the images match.

The method may further include, if the rendered image does not sufficiently match the prototype image, then continuing to evolve the parameters of the algorithm, and repeating the aforementioned steps. The method may also include using the transfer function parameters that produce a rendered image that matches the prototype image in future modifications of a 3D volume visualization image of an anatomical structure to separate desired portions thereof, using the aforementioned steps. The transfer function parameters that produce a rendered image that matches the prototype image may be used to generate views in lieu of scan technologist segmentation protocols.

In a further aspect the present invention is directed to a method of modifying a three dimensional (3D) volume visualization image of an anatomical structure in real time to separate desired portions thereof comprising providing a two dimensional (2D) image slice of a 3D volume visualization image scan of an anatomical structure, identifying a region of the 2D image slice, and providing a prototype image of desired portions of the anatomical structure. The method then includes creating a virtual histogram of the slice corresponding to the prototype image or 3D scan, with the histogram including intensity values of the identified region of the image. Using a genetic algorithm, the method then includes selecting regions of the virtual histogram and marking the selected regions with one or more virtual graphical elements, each of the graphical element comprising a genotype of the genetic algorithm. The method then includes, using a multi dimensional transfer function (MDTF), mapping optical properties to the intensity values coinciding with the prototype slice in the marked regions of the histogram to generate an image. The method further includes comparing the MDTF-generated image of the marked region with the prototype image to determine whether the MDTF-generated image of the genotype sufficiently matches the prototype image. If the MDTF-generated image sufficiently matches the prototype image, the method also includes applying the MDTF to additional 2D image slices of the 3D volume visualization image to generate a modified 3D volume visualization image of the anatomical structure.

The optical properties may comprise color and/or transparency values. The virtual histogram and the virtual graphical element may be represented mathematically. The genotype may represent the parameters of a mathematical representation that describes the virtual graphical element. The genetic algorithm may select regions of the virtual histogram by adapting genotypes to create the one or more graphical elements. The genetic algorithm may employ a B-spline for the one or more graphical elements, the B-spline having a surface defined by the parametric equation:

$$p(u,v) = \Sigma_{i=0}^{m} \Sigma_{j=0}^{n} N_{i,p}(u) n_{j,q}(v) P_{i,j};$$

whereby, $N_{i,p}(u)$ and $N_{i,q}(v)$ are the B-spline basis function of degrees p and q respectively.

The genotype represents the parametric equation that describes the B-spline of the virtual graphical element.

A pattern recognizer may be used to determine a fitness function of the genetic algorithm by evaluating whether the MDTF generated image of the genotype sufficiently matches the prototype image, and the method includes assigning a fitness value between 0.0 and 1.0 reflecting the degree at which the images match. The pattern recognizer can be a neural network model. The neural network model may be previously trained to recognize analogous images. The neural network model may be used to determine whether the MDTF generated image of the genotype sufficiently matches the prototype image, the neural network being adapted to recognize visual patterns directly from pixel images of the MDTF generated image and the prototype image. The neural network model may be used to classify whether a view is normal or abnormal and the characteristic of an abnormality extracted from the neural network model. The neural network may employ a convolution neural network model.

Alternatively, a root mean squared error (Ei) fitness function is used to determine whether MDTF generated image of the genotype sufficiently matches the prototype image, and assigning a fitness value between 0.0 and 1.0 reflecting the degree at which the images match.

If the MDTF generated image of the genotype does not sufficiently match the prototype image, the method may further include modifying the genotype to create new graphical elements, and repeating the aforementioned steps. The method may further include using the matched genotype or MDTF in future modifications of a 3D volume visualization image of an anatomical structure to separate desired portions thereof, using the aforementioned steps. The method may also include using the matched genotype or MDTF to generate views in lieu of scan technologist segmentation protocols.

In yet another aspect, the present invention is directed to a system for modifying a three dimensional (3D) volume visualization image of an anatomical structure in real time to separate desired portions thereof. The system is adapted to receive a virtual histogram of a scan, the scan based on a two dimensional (2D) image slice of a 3D volume visualization image of an anatomical structure, the histogram including intensity values of the identified region of the image. Using a genetic algorithm, the system enables marking of selected regions of the virtual histogram with one or more virtual graphical elements, each of the graphical element comprising a genotype of the genetic algorithm; using a multi dimensional transfer function (MDTF), map optical properties to the intensity values in the marked regions of the histogram. The system further enables comparison of the MDTF-generated optical properties of the marked region with the prototype image to determine whether the genotype sufficiently matches the prototype image. If the genotype sufficiently matches the prototype image, the system may apply the genotype or MDTF to additional 2D image slices of the 3D volume visualization image to generate a modified 3D volume visualization image of the anatomical structure.

A convolution neural network model may be used in the system to determine whether the MDTF generated image of the genotype sufficiently matches the prototype image, the neural network being adapted to recognize visual patterns directly from pixel images of the marked region and the prototype image.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

MODES FOR CARRYING OUT THE INVENTION

Figure 1A:
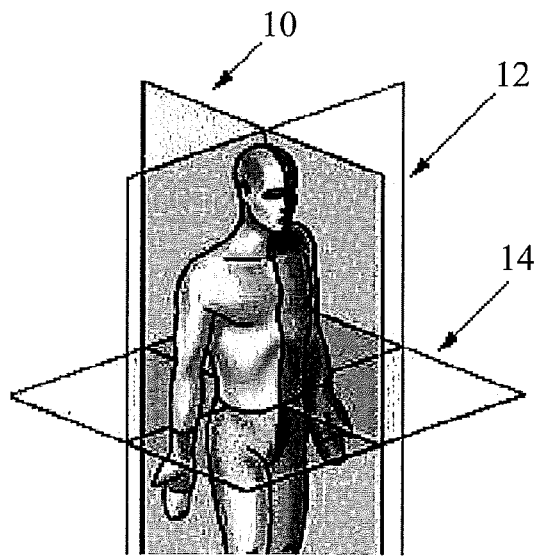
FIG. 1A is a representation of the human boy showing body orientation planes.
Figure 1B:
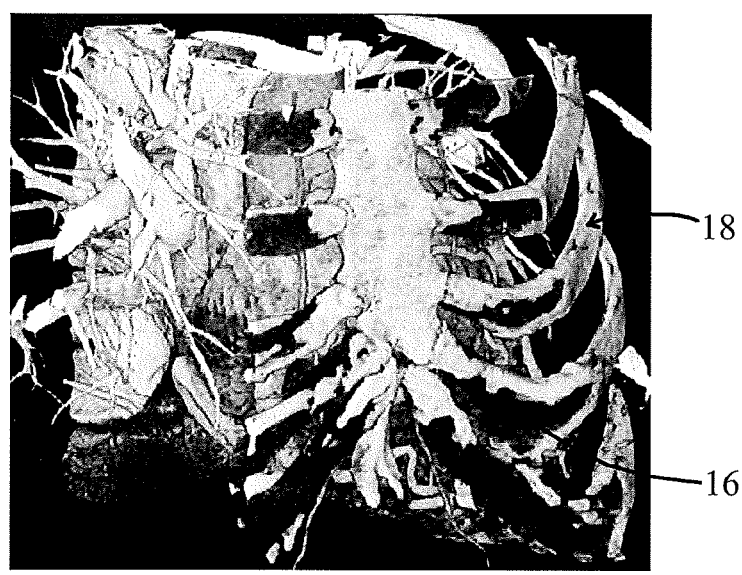
FIG. 1B is a representation of a 3D heart view obstructed by a rib cage.
Figure 1C:
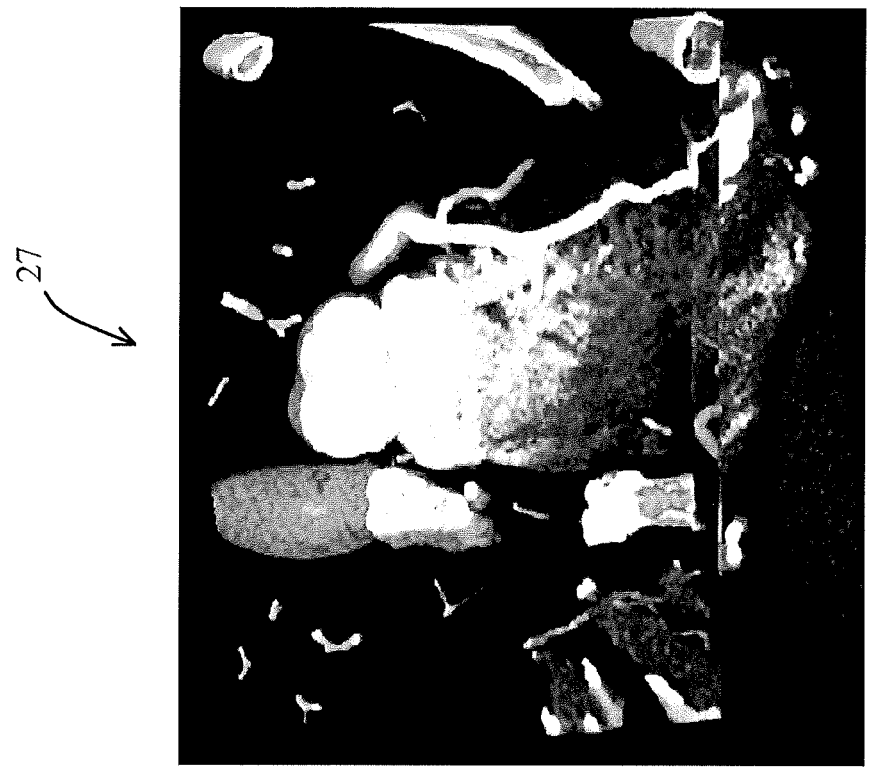
FIG. 1C is a representation of modification of FIG. 1B for rib cage removal and artery selection 30 (selected artery shown having small white dots and delineated as reference numeral 30 in image 26 segmentations to arrive at artery cross sections (image 27) as are routinely done by scanner technologists using prior art methods.
Figure 1C:
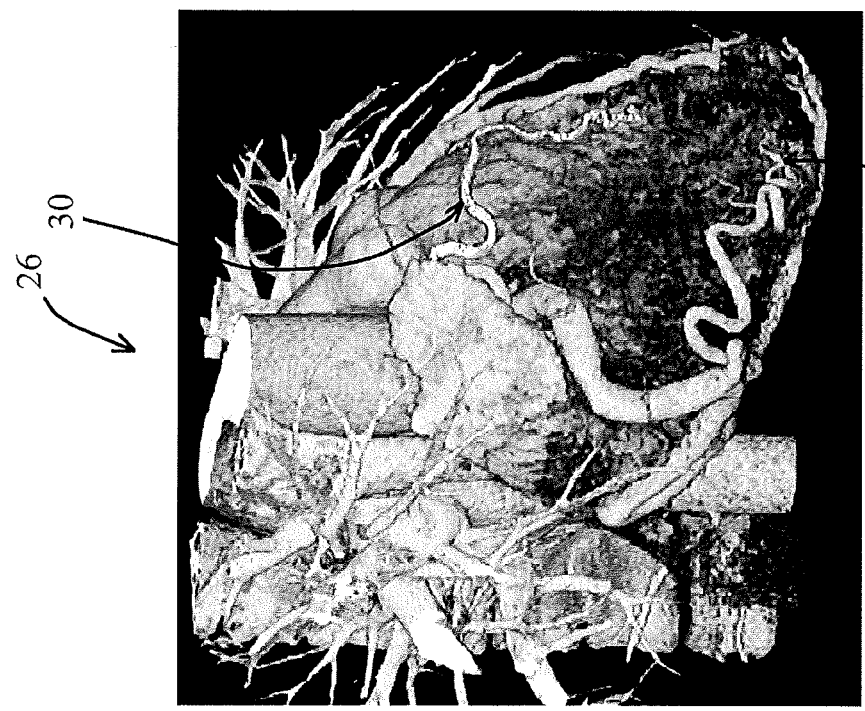
Figure 1D:
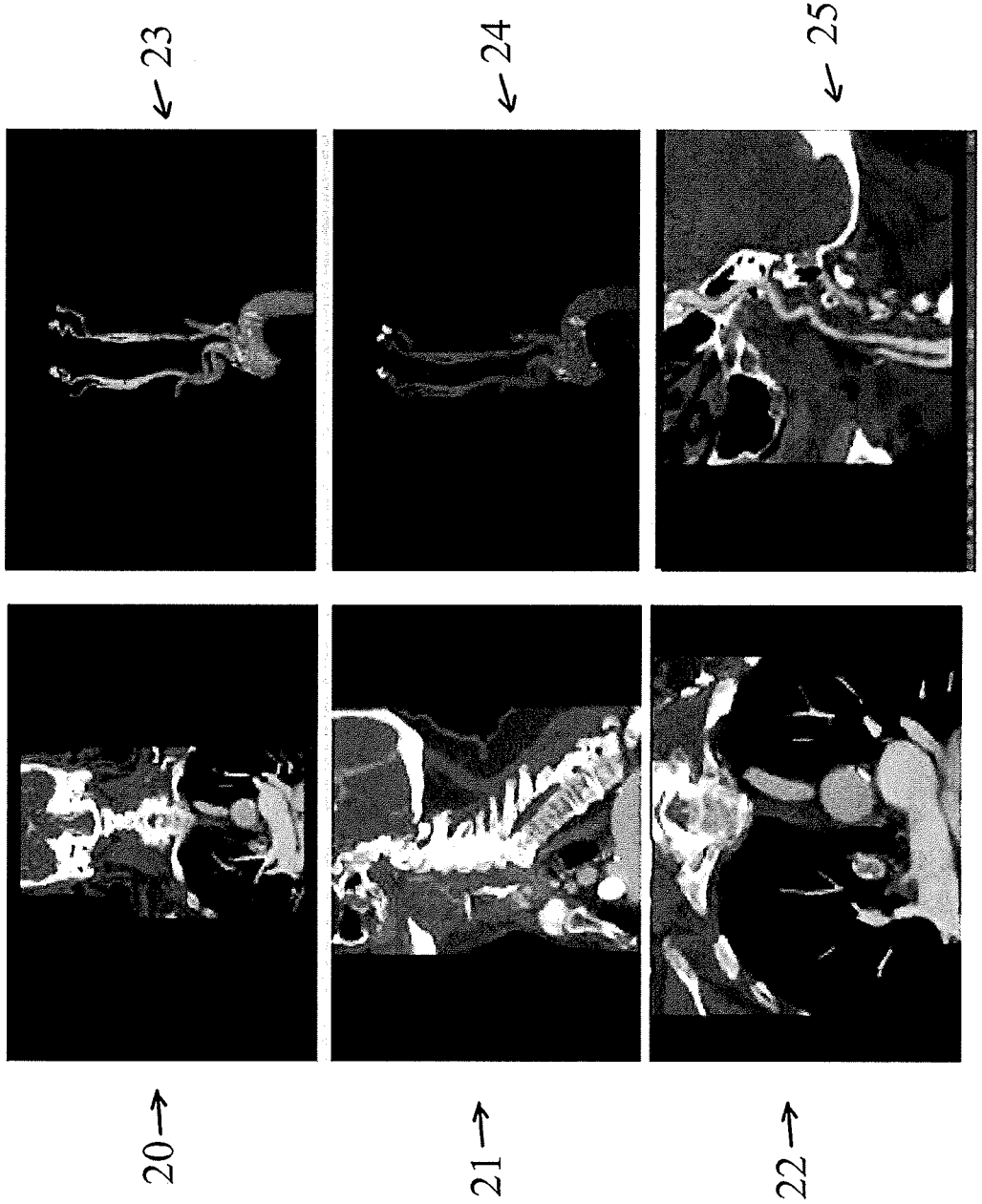
FIG. 1D is a Carotid protocol representation indicating a set of snapshots (images 20-25) of segmented CT angiography scan prepared by a technologist.

In describing the embodiment of the present invention, reference will be made herein to FIGS. 1-14 of the drawings in which like numerals refer to like features of the invention.

Medical image segmentation seeks to separate important anatomy from the image background. However, such methods are performed by a scan technician and are time consuming, and error prone. The present invention is directed to an on-demand and adaptive 3D intelligent visualization application that the physician can use to improve diagnosis and patient care without a technician's help.

Medical image segmentation seeks to change the representation of a medical scan to make it more amenable to interpretation by a physician. The extreme variability within the image requires that a scan technician be employed to separate important anatomical structures from the image background. Methods are time consuming and error prone and can lead to diagnostic inaccuracy. A solution to this problem is a semi-automatic system that is adaptive, that can learn by example, and can work in conjunction with a physician in real-time.

The present invention is directed to a physician assisted, real-time adaptive system for the segmentation of anatomical structures in 3D medical image data that completes its FDA approved medical imaging software offering. Visualization is generated when transfer function maps data intensity values in a medical scan to color and transparency values. The present invention is a Genetic Algorithm (GA) and Neural Network (NN) based adaptation technique that arrives at transfer function presets in real time. It utilizes parallel processing and adaptive algorithms preferably running on multi-core Graphics Processing Unit (GPU) processors. Subsequently, organ or disease specific clinical segmentation applications may be developed by working in collaboration with specialist.

Innovations are achieved by (i) developing an architecture that uses GPU processors to model parallel and distributed natural systems, (ii) deploying visualization methods using multi-dimensional transfer function in substitution of traditional computer vision methods of preprocessing raw data values, (iii) applying a method that uses genetic algorithms to create spline surfaces on histograms for real-time segmentation, and (iv) ultimately delivering an on-demand, adaptive and interactive segmentation visualization clinical application for a physician to effectively diagnosis a patient. Patient care is improved when diseases are detected in early stages when the scan itself might not otherwise reveal the problem without intelligent visualization.

The present invention is based on the discovery that (a) medical image segmentation is better done by visualization and artificial intelligence than by numerical computation of raw data, and (b) that the basis for on-demand intelligent visualization lies in the use of GA and NN to arrive at multi-dimensional transfer function presets.

The present invention permits a physician to create desired segmentation visualization of 3D medical scans in real time using the above system. To achieve this, the present invention provides: (I) Implementation of a parallel multi-layer convolution neural network for the recognition of segmented anatomy, (II) Automated creation of sophisticated transfer functions by adapting polynomial splines using GA and NN, and (III) Creation of a clinical segmentation application. The present invention facilitates diagnostic accuracy by delivering on-demand intelligent visualization of 3D medical scans to physicians.

The present invention is directed to physician assisted, real-time and adaptive system for the segmentation of anatomical structures in 3D medical image data. A transfer function maps intensity values to color values directly on the GPU in real-time. Carefully edited multidimensional transfer function can lead to a well segmented visualization without needing a preprocessed segmentation volume in the visualization pipeline. The system of the invention employs a Genetic Algorithm (GA) based adaptation technique that arrives at transfer function presets in real time. It utilizes parallel processing and adaptive algorithms running on multi-core Graphics Processing Unit (GPU) processors. The presets are subsequently available for reuse to build a diagnostically useful visualization of segmented anatomy within seconds during diagnosis and/or prognosis.

The 3D medical image segmentation approach of the present invention employs the following four systems and methods:

First, the system architecture uses GPU processors to model parallel and distributed natural systems. By using the hundreds of multi core processors in a GPU to simulate synapses in a neural network or DNA strand in a genetic algorithm, a massive collection of these GPUs simulates the brain or the evolution process. Difficult diagnostic medical imaging problems can be overcome using such a system.

Figure 2:
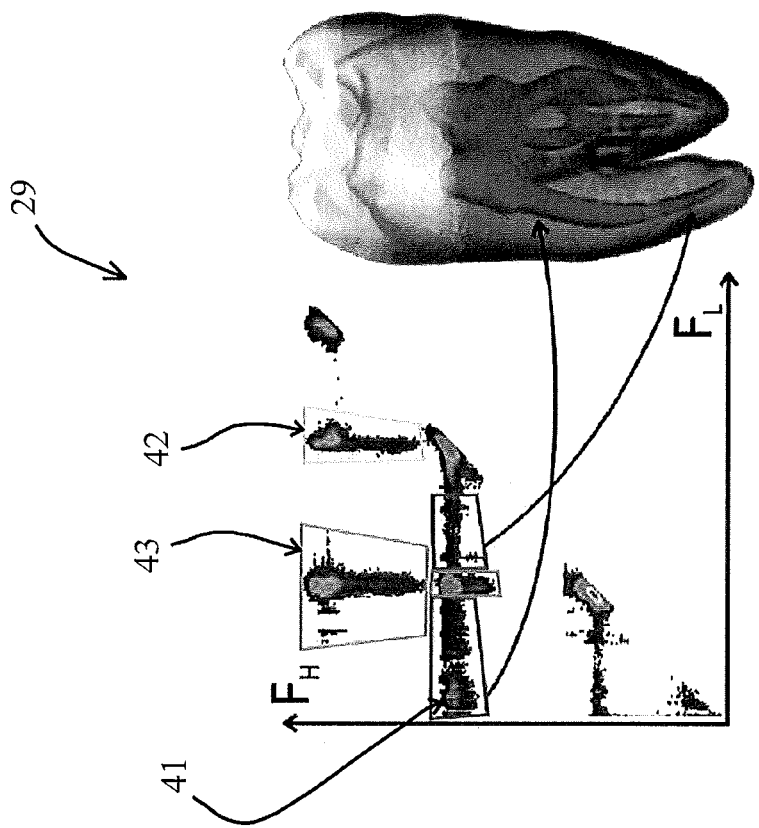
FIG. 2 is a representation of the materials that form the boundaries having distinct regions on the LH histogram and that mark those regions with polygons that can lead to a segmented volume using Multidimensional Transfer Function (MDTF). (A tooth dataset is chosen here because it contains tissues, vessel and nerves that can be hard to separate.)
Figure 2:
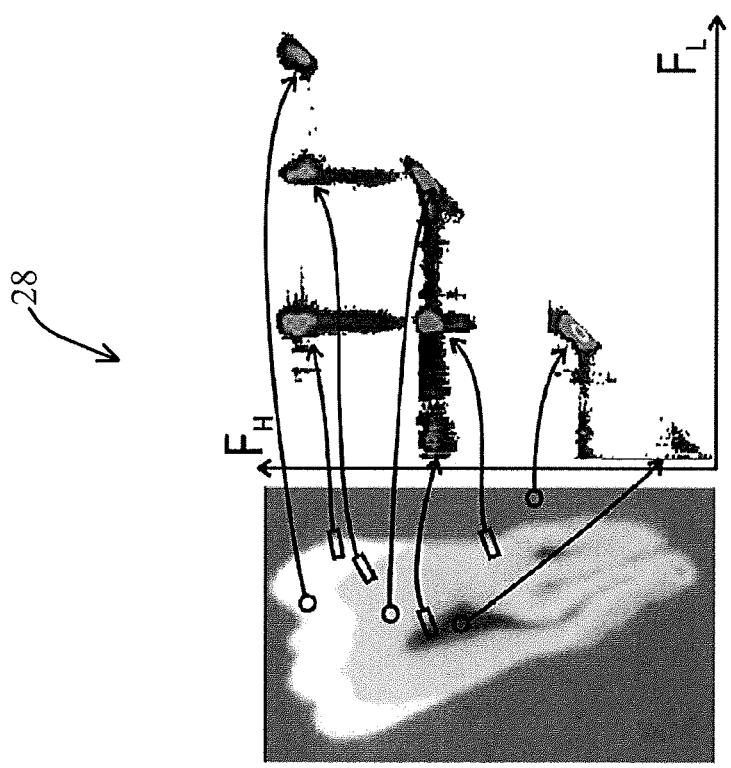

Second, segmentation of the image is directly in the visualization domain using multi dimensional transfer function (MDTF). The invention deploys visualization methods using multi-dimensional transfer function in substitution of traditional computer vision methods of preprocessing raw data values prior to visualization. Image processing based segmentation creates a burden on the visualization implementation because both the raw and its segmented volume need to be constructed and considered, adding excessive memory and computational requirements. Instead, segmentation in accordance with the present invention is represented as a MDTF directly in the visualization pipeline. The MDTF is essentially a map of color and transparency values to the intensity values in the marked regions of a histogram containing a visual representation of the distribution of data, represented by the different shading of grayscale shown in FIG. 2. It should be appreciated and understood that in accordance with the Regulations Under the Patent Cooperation Treaty, Rule 11.13 (as in force from Jul. 1, 2011), the drawings are submitted as black and white drawings only. However, it is to be appreciated and understood that the drawings are intended to include a map of color, along with the transparency values, that show the intensity values in the marked regions of a histogram as shown in FIG. 2. The histogram is created from a 2D image slice of a 3D volume visualization image of an anatomical structure, in this case, a tooth. FIG. 2 illustrates a representation of the materials that form the boundaries in a scan, which have distinct regions on the LH histogram. Marking those regions with polygons can lead to a segmented volume using MDTF. A tooth dataset is chosen here as an example because it contains tissues, vessel and nerves that can be hard to separate. In FIG. 2, image 29 (i.e., the right image) indicates regions of histogram that correspond to the segmented anatomy. For example, a first rectangle 41 (which may be shown in as a red rectangle) corresponds to the pulp, a second rectangle 42 (which may be shown as a yellow rectangle) represents the dentine, and a third rectangle 43 (which may be shown as a grey rectangle) corresponds to the enamel of the tooth. The mapping, of colored rectangular regions in the histogram space to colored images from the data domain to product visualization, is known as the transfer function. Therefore, segmentation is achieved by marking the histogram regions using polygonal widgets, i.e., graphical elements, and assigning optical properties to it. Since the marking and generation of transfer function all lie within the visualization pipeline, the present invention eliminates the need to pre-process raw scan to arrive at segmentation.

Figure 4:
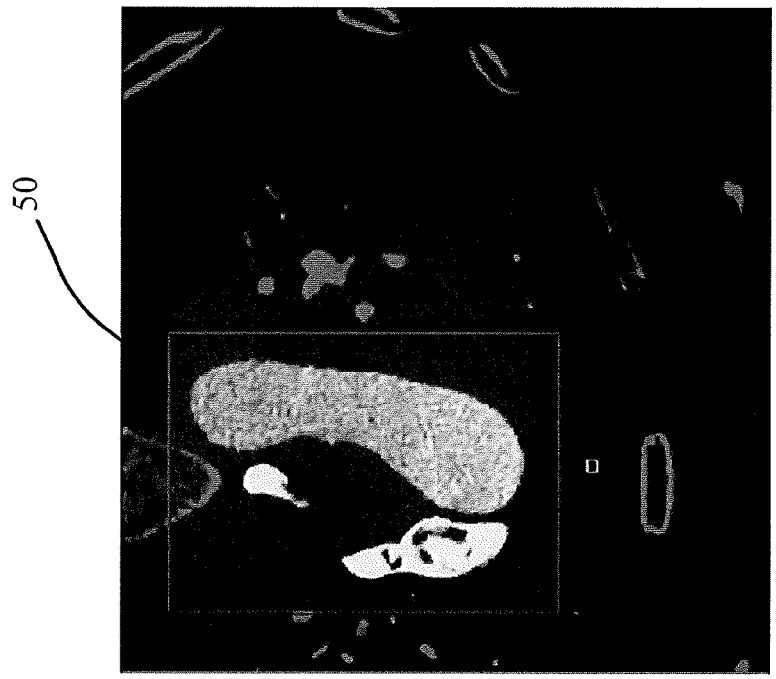
FIG. 4 is a representation of a physician's marks of a region of interest on the image of FIG. 3 in accordance with the present invention.
Figure 3:
FIG. 3 is a representation of a 2D medical image selected in accordance with the present invention.

Third, a real time adaptive B-spline is used to mark histograms of a region of interest on the 2D image. The method of the present invention uses genetic algorithms to create spline surfaces on a virtual multi-dimensional histogram for real-time segmentation. Crafting a multidimensional transfer functions by creating polygonal widgets on a histogram surface is an idiosyncratic manual method that is impractical in medical practice. Moreover, polygonal widgets used to select histograms lack the flexibility to snug fit in to interior points of a histogram feature map. The segmentation process is initiated by marking a region of interest on a prototype 2D image slice using a more familiar user interface, as shown in FIGS. 3 and 4. FIG. 3 is a representation of a 2D medical image selected in accordance with the present invention, and FIG. 4 is a representation of a physician's marks of a region of interest on the image of FIG. 3 in accordance with the present invention.

Figure 6:
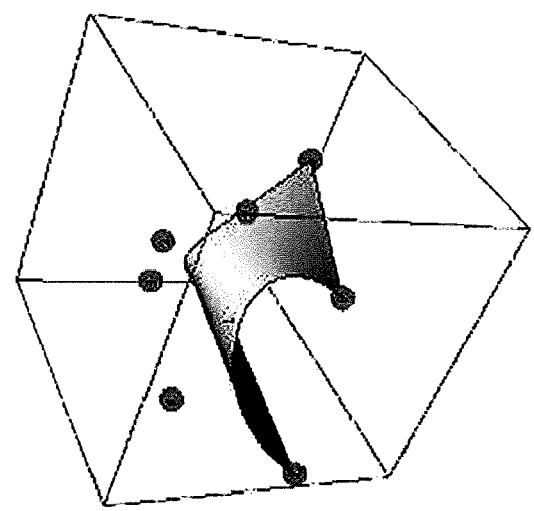
FIG. 6 is a representation of B-spline surface generated in connection with the image of FIGS. 4 and 5 in accordance with the present invention.
Figure 5:
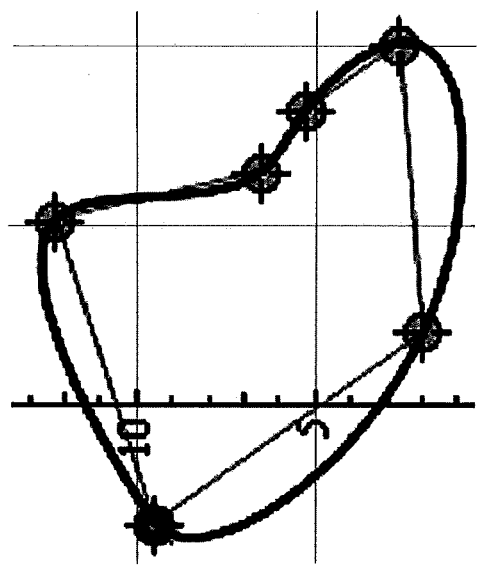
FIG. 5 is a representation of a B-spline curve generated in connection with the image of FIG. 4 in accordance with the present invention.

A virtual multi-dimensional histogram of the 2D image scan is then constructed on demand. The GA implementation adapts genes to create widgets that select the histogram regions. The materials that form the boundaries in a scan have distinct regions on a histogram, whereby marking those regions with polygons can lead to a segmented volume using MDTF (FIG. 2). A B-spline is employed as a basis of the widgets because altering its control points enables the creation of shapes with greater flexibility, as shown in FIGS. 5 and 6. A B-spline (named after Bézier) is a mathematical model used in computer graphics for generating and representing curves and surfaces, and is represented with control points lying off the curve itself. FIG. 5 is an example representation of a B-spline curve that can get generated by the GA to form the widget that specifies a region of a virtual 2D histogram in accordance with the present invention. FIG. 6 is an example representation of B-spline surface that can get generated by the GA to form the widget that specifies a region and its interior points of a virtual histogram in accordance with the present invention. Again, it should be appreciated and understood that this B-spline surface is preferably depicted to include a map of color. A genotype of the GA would describe one or many B-spline surfaces. Each B-spline curve will be indicated by describing a set of control points (e.g., control points 1-7 as shown in FIG. 6) as coordinates and the degrees of the B-spline curves/basis function. The GA can essentially generate any shape by changing the control points or degrees. The GA acts as an evolver to evolve parameters of an algorithm that employs MDTF to map optical properties to intensity values coinciding with the portions of the anatomical structure of interest.

Each genotype is visualized and matched against the prototype image using a convolution neural network (CNN). The fitness of a genome is a function of how well the visualization matches the prototype image. Upon a successful match, the genome is applied on the entire scan to generate a 3D visualization. GPU implementation of the GA and CNN ensures interactive response of the segmentation. A physician correlates the visualization to an anatomical structure and the genome is saved as a preset that can be recalled when needed. This stochastic natural selection approach to determining B-spline surface on multi-dimensional histograms can lead to a discovery about medical image segmentation that cannot be achieved using existing techniques.

Figure 7:
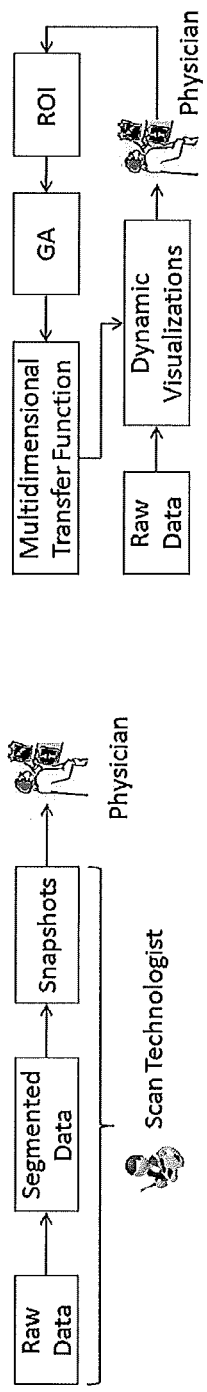
FIG. 7 is a comparison of segmentation approaches of the prior art (right) with that of the present invention (left).

Fourth, the present invention delivers on-demand, adaptive and interactive segmentation visualization that can enable physician to diagnosis a patient scan effectively to improve the patient's care. FIG. 7 is a comparison of segmentation approaches of the prior art (right) with that of the present invention (left). In the conventional prior art method, (not real-time), a scan technologist segments the volume, and then creates snapshots for physicians to use in diagnosis. In the method of the present invention (real-time), a physician sets a region of interest (ROI) and GA adapts to match structures in ROI to present dynamic visualizations. In the present invention, physicians manipulate raw scans directly to create effective visualizations. This improves patient care when diseases are detected in early stages when the scan itself might not otherwise reveal the problem without intelligent visualization. Survival rate after early stage diagnosis and treatment of a cancer patient can be about ninety percent.

Implementation of a parallel multi-layer convolution neural network for the recognition of segmented anatomy may be described as follows:

The performance of a GA is evaluated by having a multi-layer convolution neural network (MCNN) match the output of the GA produced by a gene with the prototype image specified by a user. A match or lack thereof is indicative of the fitness value of a genotype. The best-fit found will reflect the appropriate multi-dimensional transfer function that matches the prototype.

Figure 8:
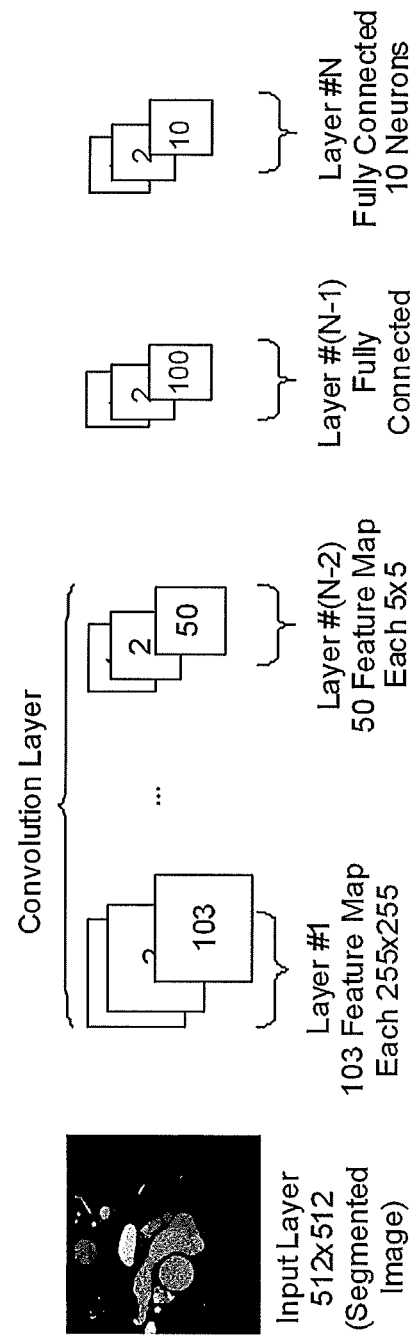
FIG. 8 is a representation of a multi-layer convolution neural network (MCNN) model employed in accordance with the present invention.
Figure 9:
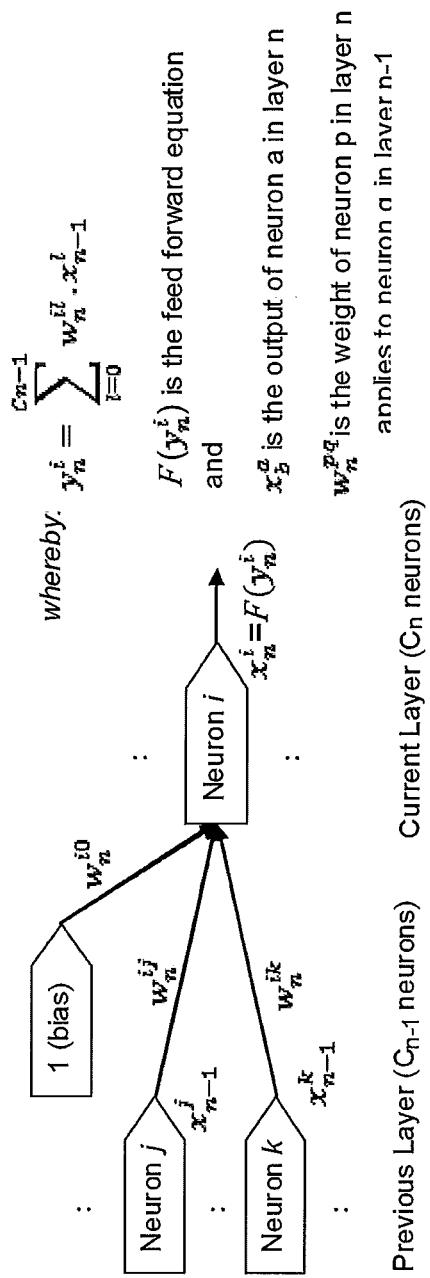
FIG. 9 is representation of an overview of i-th neuron in the multi-layer convolution neural network (MCNN) model employed in accordance with the present invention.

MCNN employed in the present invention is a neural network trained with a version of the back-propagation algorithm. It is designed to recognize visual patterns directly from pixel images with minimal preprocessing. A MCNN can recognize patterns with extreme variability (such as handwritten characters), and with robustness to distortions and simple geometric transformations. A MCNN is illustrated in FIG. 8, which is a representation of a multi-layer convolution neural network (MCNN) model employed in accordance with the present invention. The input layer may be a 512×512 segmentation image, and the output layer may be composed of ten neurons of which exactly one neuron with value of $\{+1\}$ (the answer) while all other nine neurons with value of $\{-1\}$. FIG. 9 depicts a neuron and its connections, and is representation of an overview of i-th neuron in the multi-layer convolution neural network (MCNN) model employed in accordance with the present invention. Each neuron calculates a weighted sum of inputs and compares it to a bias. If the sum is higher than the bias, the output is set to $\{+1\}$, otherwise to $\{-1\}$. The convolution layers' weights are all tied together thereby reducing the number of free parameters to train, and they detect shifting within the image.

Figure 10:
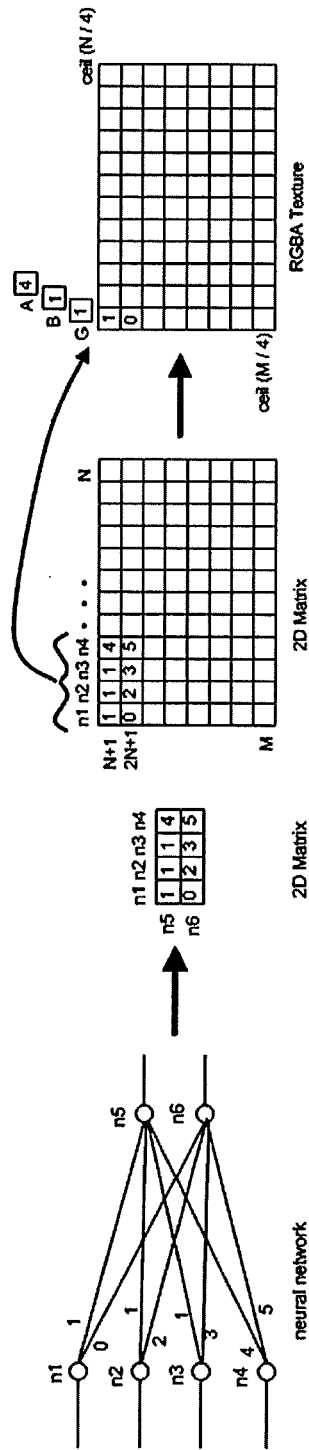
FIG. 10 is a representation of a MCNN layer, connection, neuron, and its weight represented as a matrix of M output by N input in the multi-layer convolution neural network (MCNN) model employed in accordance with the present invention.

MCNN requires a considerable number of vector and matrix operations and therefore very suitable to be implemented in a parallel programming model and run on GPUs, as shown in FIG. 10. FIG. 10 is a representation of a MCNN layer, connection, neuron, and its weight represented as a matrix of M output by N input in the multi-layer convolution neural network (MCNN) model employed in accordance with the present invention.

The training of the Neural Network is done using Back Propagation implemented on the GPU. Training of the network involves adjustment of weights (W) to match the actual outputs to desired outputs of the network [20]. The learning process consists in the finding the value of W that minimizes the Mean Squared Error (MSE).

The genotype in a GA would represent one or many B-spline surfaces. Each B-spline surface will be indicated by describing a set of control points as coordinates and the degrees of the B-spline curves/basis function. The creation of 2D histogram (FIG. 2) can be time consuming because it involves projecting millions of rays through the scan to build the histogram. However, the histogram is only necessary for a human to draw polygonal regions on, to specify the transfer function through visual inspection. Since the GA of the present invention is producing B-splines representation that is a set of virtual polygonal regions (mathematical parametric representation), the histogram creation will be omitted because it too can be virtual, significantly accelerating the visualization pipeline. The GA algorithm is an adaptive stochastic model that selects a virtual 2D histogram, whose result is compared to prototype image to derive fitness of a match. The GA's best fit reflects a transfer function that is applied to the entire scan to arrive at the desired segmentation. The GA can essentially generate any shape by changing the control points or degrees. Two or more B-spline surfaces are used so multiple anatomies within a scan can be segmented. The B-spline surface is defined by the parametric equation:

$$p(u,v) = \Sigma_{i=0}^{m} \Sigma_{j=0}^{n} N_{i,p}(u) N_{j,q}(v) P_{i,j};$$

whereby, $N_{i,p}(u)$ and $N_{j,q}(v)$ are the B-spline basis function of degrees p and q respectively.

Each member of the GA population above is retrieved and each genome is parsed to create visualization. The spline's parametric equations are represented as matrices and are efficiently implemented using a GPU to get interpolated point on the surface. The point is then used to sample the histogram. In summary, a genotype creates a feature selection map on the histogram and ultimately describes a transfer function. The optical properties of the transfer function are applied to the medical scan to visualize the segmentation. The resulting image is recognized using MCNN and categorized as whether the desired segmentation has been achieved. The GPU implementation of Neural Network architecture is sufficient for recognizing an intermediary input image with the prototype image of a user selection in real-time. If the result is positive, the genome is noted to be highly fit and the genome is saved. If on the other hand, the result is negative, the fitness value is computed by evaluating the MSE in the MCNN network and the genotype is further adapted and modified by the GA. The MCNN provides a sophisticated way to measure the fitness function of the GA.

The MCNN way of generating fitness function can be omitted by using a more simple root mean squared error (Ei) fitness function. The Ei represents the degree of difference between the GA generated visualization and the prototype region of interest image selected by the physician.

A set of B-spline surfaces applied on a multi-dimensional histogram generated under adaptive pressure of a GA can pick out anatomical structures. Such segmentation can be saved as presets and later recalled to display the desired anatomy.

When a genetic algorithm and neural network is ran on a massively large GPU cluster, the present invention mimics a natural system. The present invention mimics how evolution works by creating massive population in genetic algorithm; the population evolves quickly in real time and the fittest survive. The present invention also mimics how the brain works by simulating a large number of "synapses/neuron" in a neural network. A single AMD 6990 GPU has 3072 cores/stream processors. Multiple GPUs combined through patent Ser. No. 11/672,581 can provide massively scalable GPU platform to create large amount of population or "synapses/neurons" that mimics a natural system to solve the problem of modifying a 3D volume visualization image of an anatomical structure in real time to separate desired portions thereof. The system described in PCT/US2010/036355 is a system that may enable this. In accordance with the present invention, a genetic algorithm can stochastically arrive at an answer, i.e. the best solution (depending on how long one lets the population evolve) to the question of what is the best widget to select the histogram to derive transfer function that is best fit to prototype image or what is the best parameter of a compression algorithm to choose what enables the highest compression while still maintaining diagnostic quality. Also, the present invention uses neural network to learn what is a normal and abnormal case so that one may develop algorithms to alert physicians of abnormality that the physician may have missed—not necessarily to provide diagnosis but to alert the physician of an abnormal structure that may have been missed by the physician.

Figure 11:
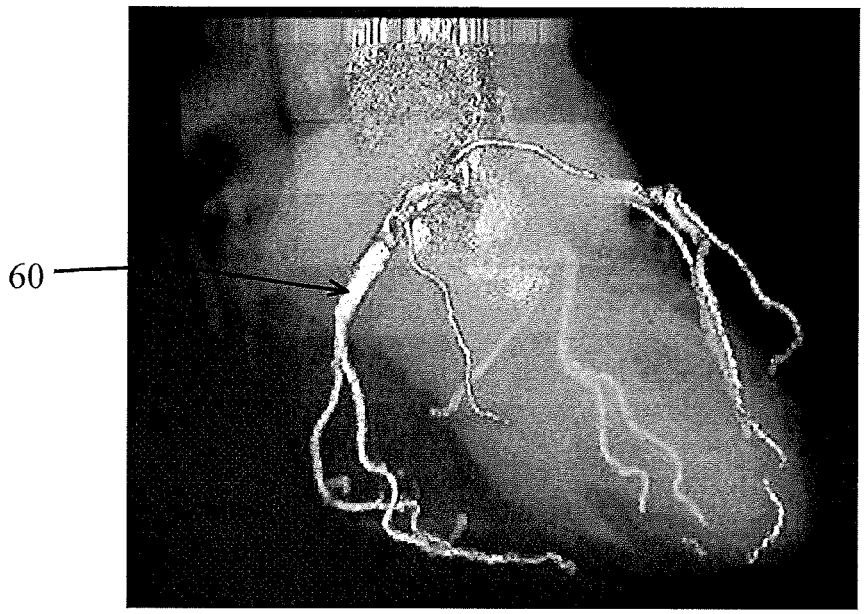
FIG. 11 is a representation of a visualization of the coronary circulation blood vessels for the diagnosis of heart function and blockage analysis. (A stent on the right coronary artery is visible.)
Figure 12:
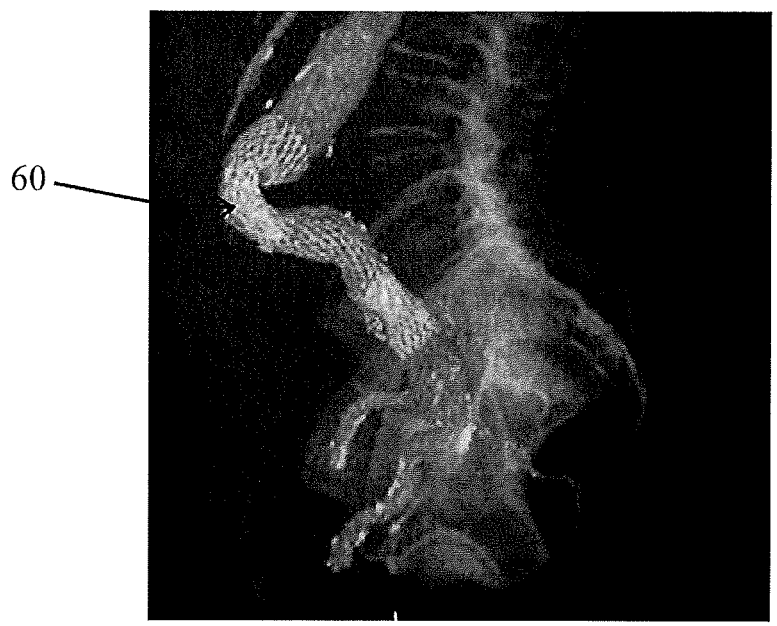
FIG. 12 is a representation of a visualization of a stent in the lower extremity to help in the care of patient with coronary arterial blockage.
Figure 13:
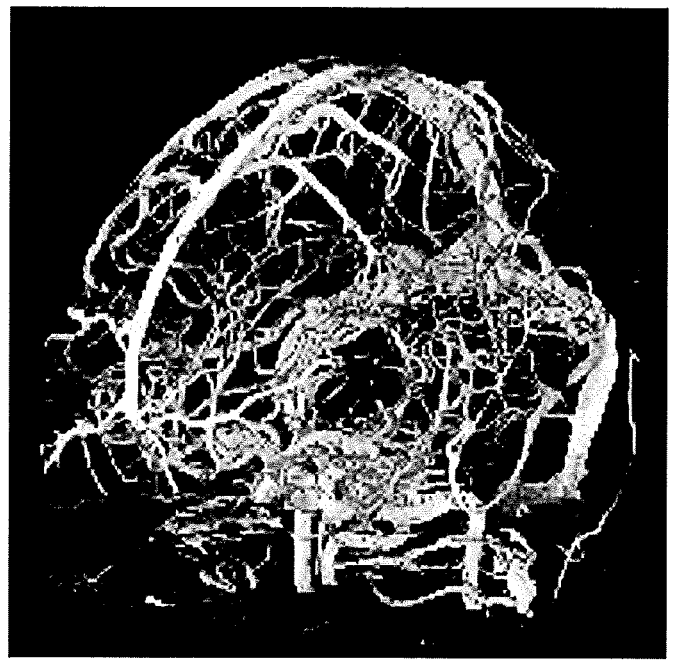
FIG. 13 is a representation of a visualization of blood vessels of a brain is enabled by the removal of the skull.
Figure 14:
FIG. 14 is a representation of a visualization of a breast cancer. (This patient overcame the disease and avoided a Mastectomy through early detection and proper care.)

A clinical segmentation application may be described as follows:

Critical care ranges from heart, vascular to cancer diseases. Examples of clinically relevant advanced visualization are shown by FIGS. 11, 12, 13 and 14. These images were derived from a technician using current manual methods for segmentation. FIG. 11 is a representation of a visualization of the coronary circulation blood vessels for the diagnosis of heart function and blockage analysis. A stent 60 on the right coronary artery is visible. FIG. 12 is a representation of a visualization of a stent 60 in the lower extremity to help in the care of patient with coronary arterial blockage. FIG. 13 is a representation of a visualization of blood vessels of a brain, which is enabled by the removal of the skull. FIG. 14 is a representation of a visualization of a breast cancer (as depicted by the white arrow within such image). This patient overcame the disease and avoided a Mastectomy through early detection and proper care.

Once incorporated in to the physician's workflow, the visualizations in FIGS. 11-14 are readily producible by the method and system of the present invention. The invention also includes generating clinical tools for segmentation tasks. The segmentation engine described above may be integrated with the web portal platforms so it can be accessed over the Internet or other network during a diagnosis or prognosis. An example of such web portal platform is disclosed in PCT application no. PCT/US2010/036355, filed on May 27, 2010, entitled "Method and System for Fast Access to Advanced Visualization of Medical Scans Using a Dedicated Web Portal," the disclosure of which is hereby incorporated by reference. A physician would begin using the segmentation engine and communicate to the web portal platform on the specialized tools that the physician needs to effectively perform the visualization in real-time. The requirements of the physician are incorporated into the clinical tools.

During the segmentation, the genome that matched a desired segmentation is saved as a preset. Physicians may reuse these presets to build a diagnostically useful visualization within seconds during prognosis. For example, a referring physician may wish to communicate an aneurysm to a patient. The physician may select a preset that removes the skull from the scan, one that highlights the vessels, while contextually showing the brain as a translucent matter. The present invention includes methods to incorporate such said presets in to the diagnosis impression and make it accessible through the standard reporting workflow.

The present invention also defines a set of supported preliminary radiology reading protocols, such as "brain aneurysm reading protocol" for the visualization of the vessels of the brain. This will enable successful implementation for diagnosis use. A physician will be able to use the clinical tools of the present invention to arrive at a desired advanced visualization for a predefined set of radiology reading protocols without the intervention of technologists.

The present invention provides a method and system for modifying a 3D volume visualization image of an anatomical structure in real time to separate desired portions thereof, which may be distributed in one or more functional components or modules. The present invention may be embodied as a system, method or computer program product. The present invention may take the form of an entirely hardware embodiment, an entirely software embodiment (including firmware, resident software, micro-code, etc.) or an embodiment combining software and hardware aspects that may all generally be referred to herein as a "circuit," "module" or "system." The present invention may take the form of a computer program product embodied in one or more computer readable medium(s) having computer readable program code embodied thereon. Program code embodied on a computer readable medium may be transmitted using any appropriate medium, including but not limited to wireless, wireline, optical fiber cable, radio frequency (RF) or the like, or any suitable combination of the foregoing. In particular, one or more remote client applications (e.g., remote computers) may be connected to a centralized server application, and a 2D view of interest may be identified on the remote client application, and one or more, or all, of the other operations may be performed on the centralized server application. The remote client application is then provided with the final view, whether normal or abnormal, or a flag or warning of same.

Computer program code for carrying out operations for the method and other aspects of the present invention may be written in any combination of one or more programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the function blocks or modules in the drawings.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the function blocks or modules in the drawings.

Communication and transmission connections between the individual system components or modules, as well as with the server and users, may be made by wireless, wireline, optical fiber cable, radio frequency (RF) or the like, and may also be made via an internal network (LAN), wide area network (WAN) and/or over the Internet or other connection means. The individual system components may be incorporated as hardware or software modules within a computer. The user may employ an otherwise conventional web browser application on a computer or other electronic device at a remote location capable of communicating across an intranet or the Internet, which device also may have connection with a local computer-readable storage medium that may be used as the customer's data source. A suitable storage medium may be employed to receive all or portions of volume visualization dataset(s) such as CT or MRI scans made elsewhere, and function as a transmitter of such dataset(s) to a centralized database, as will be discussed further below. Such storage medium may also be employed to receive and store downloads from the centralized database of all or portions of volume visualization dataset(s) or views created there from. One or more computer readable medium(s) may be utilized, alone or in combination. A suitable computer readable storage medium may be, for example, but not limited to, an electronic, magnetic, optical, electromagnetic, infrared, or semiconductor system, apparatus, or device, or any suitable combination of the foregoing. Other examples of suitable computer readable storage medium would include, without limitation, the following: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (e.g., CD-ROM), an optical storage device (e.g., DVD ROM), a magnetic storage device (e.g., diskette), or any suitable combination of the foregoing. A suitable computer readable storage medium may be any tangible medium that can contain, or store a program for use by or in connection with an instruction execution system, apparatus, or device.

Thus, the present invention provides one or more of the following advantages:

1) Encapsulating multidimensional properties as a transfer function through physician guided adaptive algorithms running on a GPU alienates anatomical structures from each other automatically and in real-time. This enables Physicians to control the views they generate during diagnosis. This provides better prognosis and ultimately enhanced patient care.

2) These techniques can assist diagnosticians to identify cardiac, vessel, and cancer diseases in early stages when the scan itself might not otherwise reveal the problem without advanced visualization.

3) 3D visualization provides deeper understandings through familiar biological visualizations of anatomical structures thus improves radiological reads, saves time to enable more reads per day and cuts costs.

Diagnostic accuracy can be facilitated when combined with existing FDA approved web portal platform, such as that described in the aforementioned PCT application, so that intelligent visualization can be accessed over the Internet or other network, and on demand.

While the present invention has been particularly described, in conjunction with a specific embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of modifying a three dimensional (3D) volume visualization image of an anatomical structure in real time to separate desired portions thereof comprising:
  providing a two dimensional (2D) image slice of a 3D volume visualization image of an anatomical structure;
  identifying portions of the anatomical structure of interest;
  providing a prototype image of desired portions of the anatomical structure;
  using an evolver to evolve parameters of an algorithm that employs a transfer function to map optical properties to intensity values coinciding with the portions of the anatomical structure of interest to generate an image that sufficiently matches the prototype image;
  if the parameters match the prototype image, applying the transfer function to additional 2D image slices of the 3D volume visualization image to generate a modified 3D volume visualization image of the anatomical structure.

2. The method of claim 1 wherein the optical properties comprise color and/or transparency values.

3. The method of claim 1 wherein the evolver is a genetic algorithm.

4. The method of claim 3 wherein a pattern recognizer is used to determine a fitness function of the genetic algorithm by evaluating whether the transfer function generated image sufficiently matches the prototype image, and assigning a fitness value between 0.0 and 1.0 reflecting the degree at which the images match.

5. The method of claim 4 wherein the pattern recognizer is a neural network model.

6. The method of claim 5 wherein the neural network model has been previously trained to recognize analogous images.

7. The method of claim 1 wherein the parameter values define a set of graphical elements selecting a histogram.

8. The method of claim 1 wherein the algorithm employs graphical elements selecting a histogram to generate a transfer function.

9. The method of claim 1 wherein a pattern recognizer is used to determine whether the view is flagged as normal or abnormal by the centralized server application and identifies the anomaly in the view.

10. The method of claim 1 wherein a neural network model is used to determine whether the transfer function generated image matches the prototype image, the neural network being adapted to recognize visual patterns directly from pixel images of the transfer function generated image and the prototype image.

11. The method of claim 1 wherein the neural network employs a convolution neural network model.

12. The method of claim 1 wherein a root mean squared error (Ei) fitness function is used to determine whether the transfer function generated image sufficiently matches the prototype image, and assigning a fitness value between 0.0 and 1.0 reflecting the degree at which the images match.

13. The method of claim 1 further including, if the transfer function generated image does not sufficiently match the prototype image, then continue evolving the parameters of the algorithm, and repeating the aforementioned steps.

14. The method of claim 1 further including using the matched genotype or transfer function in future modifications of a 3D volume visualization image of an anatomical structure to separate desired portions thereof, using the aforementioned steps.

15. The method of claim 1 further including using the matched genotype or transfer function to generate views in lieu of scan technologist segmentation protocols.

16. A method of displaying adaptive visualization on a remote client application and a three dimensional (3D) volume visualization image at centralized server application thereof comprising:
   providing a two dimensional (2D) image slice of a 3D volume visualization image of an anatomical structure;
   identifying a view of interest on the remote client application;
   transmitting view of interest information to the centralized server application;
   using an evolver to evolve transfer-function-parameters of an algorithm that maps optical properties to intensity values to produce a view of interest in the form of a rendered image;
   using an evolver to evolve compression-parameters of an algorithm that optimizes the compression algorithm to compress the rendered image;
   using an evolver to evolve transmission-parameters of an algorithm that optimizes the transmission of the compressed image from the centralized server to the remote client application.

17. The method of claim 16 wherein the optimization of compression-parameters produces the highest compression ratio while maintaining diagnostic quality.

18. The method of claim 16 wherein the optimization of transmission-parameters produces the fastest transmission to the remote client application.

19. The method of claim 16 wherein the evolver is a genetic algorithm.

20. The method of claim 16 wherein the transfer-function-parameter values define a set of graphical elements selecting a histogram.

21. The method of claim 16 wherein the algorithm employs graphical elements selecting a histogram to generate the transfer-function-parameters.

22. The method of claim 16 wherein a pattern recognizer is used to determine a fitness function of a genetic algorithm by evaluating whether the rendered image sufficiently matches the view of interest, and assigning a fitness value between 0.0 and 1.0 reflecting the degree at which the images match.

23. The method of claim 16 wherein a pattern recognizer is used to determine whether the view is flagged as normal or abnormal by the centralized server application.

24. The method of claim 23 wherein the pattern recognizer is a neural network model.

25. The method of claim 24 wherein a neural network model has been previously trained to recognize analogous rendered images.

26. The method of claim 16 wherein a pattern recognizer is used to determine whether the view is flagged as normal or abnormal by the centralized server application and identifies the anomaly in the view.

27. The method of claim 16 wherein a neural network model is used to determine whether the rendered image matches the prototype image, the neural network being adapted to recognize visual patterns directly from pixel images of the rendered image and the prototype image.

28. The method of claim 27 wherein the neural network employs a convolution neural network model.

29. The method of claim 28 wherein the neural network model has been previously trained to recognize normal or abnormal views.

30. The method of claim 16 wherein a flag or warning is sent to the remote client application to alert a user as to whether the view is normal or abnormal.

31. The method of claim 30 wherein the abnormal section of the view is identified and sent to the remote client application to alert a user.

32. The method of claim 31 wherein the user is a radiologist.

33. The method of claim 31 wherein the user is a physician.

34. The method of claim 16 wherein a root mean squared error (Ei) fitness function is used to determine whether the rendered image sufficiently matches the prototype image, and assigning a fitness value between 0.0 and 1.0 reflecting the degree at which the images match.

35. The method of claim 16 further including, if the rendered image does not sufficiently match the prototype image, then continue evolving the parameters of the algorithm, and repeating the aforementioned steps.

36. The method of claim 16 further including using the transfer function parameters that produce a rendered image that matches the prototype image in future modifications of a 3D volume visualization image of an anatomical structure to separate desired portions thereof, using the aforementioned steps.

37. The method of claim 16 further including using the transfer function parameters that produce a rendered image that matches the prototype image to generate views in lieu of scan technologist segmentation protocols.

38. A method of modifying a three dimensional (3D) volume visualization image of an anatomical structure in real time to separate desired portions thereof comprising:
   providing a two dimensional (2D) image slice of a 3D volume visualization image scan of an anatomical structure;
   identifying a region of the 2D image slice;
   providing a prototype image of desired portions of the anatomical structure;

creating a virtual histogram of the slice corresponding to the prototype image or 3D scan, the histogram including intensity values of the identified region of the image;

using a genetic algorithm, selecting regions of the virtual histogram and marking the selected regions with one or more virtual graphical elements, each of the graphical element comprising a genotype of the genetic algorithm;

using a multi dimensional transfer function (MDTF), mapping optical properties to the intensity values coinciding with the prototype slice in the marked regions of the histogram to generate an image;

comparing the MDTF-generated image of the marked region with the prototype image to determine whether the MDTF-generated image of the genotype sufficiently matches the prototype image;

if the MDTF-generated image sufficiently matches the prototype image, applying the MDTF to additional 2D image slices of the 3D volume visualization image to generate a modified 3D volume visualization image of the anatomical structure.

39. The method of claim 38 wherein the optical properties comprise color and/or transparency values.

40. The method of claim 38 wherein the virtual histogram is represented mathematically.

41. The method of claim 38 wherein the virtual graphical element is represented mathematically.

42. The method of claim 38 wherein the genotype represents the parameters of a mathematical representation that describes the virtual graphical element.

43. The method of claim 38 wherein the genetic algorithm selects regions of the virtual histogram by adapting genotypes to create the one or more graphical elements.

44. The method of claim 38 wherein the genetic algorithm employs a B-spline for the one or more graphical elements.

45. The method of claim 38 wherein the genetic algorithm employs a B-spline for the one or more graphical elements, the B-spline having a surface defined by the parametric equation:

$$p(u, v) = \Sigma_{i=0}^{m} \Sigma_{j=0}^{n} N_{i,p}(u) N_{j,q}(v) P_{i,j};$$

whereby, $N_{i,p}(u)$ and $N_{j,q}(v)$ are the B-spline basis function of degrees p and q respectively.

46. The method of claim 38 wherein the genotype represents the parametric equation that describes the B-spline of the virtual graphical element.

47. The method of claim 38 wherein a neural network model is used to determine a fitness function of the genetic algorithm by evaluating whether the MDTF generated image of the genotype sufficiently matches the prototype image, and assigning a fitness value between 0.0 and 1.0 reflecting the degree at which the images match.

48. The method of claim 47 wherein the neural network model has been previously trained to recognize analogous images.

49. The method of claim 38 wherein a neural network model is used to determine whether the MDTF generated image of the genotype sufficiently matches the prototype image, the neural network being adapted to recognize visual patterns directly from pixel images of the MDTF generated image and the prototype image.

50. The method of claim 49 wherein the neural network employs a convolution neural network model.

51. The method of claim 38 wherein a view of interest is in the form of a MDTF generated image and a neural network model is used to determine whether the view is flagged as normal or abnormal by the centralized server application.

52. The method of claim 51 wherein the neural network model has been previously trained to recognize normal or abnormal views.

53. The method of claim 51 wherein a flag or warning is sent to the remote client application to alert a user as to whether the view is normal or abnormal.

54. The method of claim 53 wherein the abnormal section of the view is identified and sent to the remote client application to alert a user.

55. The method of claim 54 wherein the user is a radiologist.

56. The method of claim 54 wherein the user is a physician.

57. The method of claim 38 wherein a root mean squared error (Ei) fitness function is used to determine whether MDTF generated image of the genotype sufficiently matches the prototype image, and assigning a fitness value between 0.0 and 1.0 reflecting the degree at which the images match.

58. The method of claim 38 further including, if the MDTF generated image of the genotype does not sufficiently match the prototype image, then modifying the genotype to create new graphical elements, and repeating the aforementioned steps.

59. The method of claim 38 further including using the matched genotype or MDTF in future modifications of a 3D volume visualization image of an anatomical structure to separate desired portions thereof, using the aforementioned steps.

60. The method of claim 38 further including using the matched genotype or MDTF to generate views in lieu of scan technologist segmentation protocols.

61. A system for modifying a three dimensional (3D) volume visualization image of an anatomical structure in real time to separate desired portions thereof, the system adapted to receive a virtual histogram of a scan, the scan based on a two dimensional (2D) image slice of a 3D volume visualization image of an anatomical structure, the histogram including intensity values of the identified region of the image; using a genetic algorithm, enable marking of selected regions of the virtual histogram with one or more virtual graphical elements, each of the graphical element comprising a genotype of the genetic algorithm; using a multi dimensional transfer function (MDTF), map optical properties to the intensity values in the marked regions of the histogram; enable comparison of the MDTF-generated optical properties of the marked region with the prototype image to determine whether the genotype sufficiently matches the prototype image; and if the genotype sufficiently matches the prototype image, apply the genotype or MDTF to additional 2D image slices of the 3D volume visualization image to generate a modified 3D volume visualization image of the anatomical structure.

62. The system of claim 61 wherein a convolution neural network model is used to determine whether the MDTF generated image of the genotype sufficiently matches the prototype image, the neural network being adapted to recognize visual patterns directly from pixel images of the marked region and the prototype image.

* * * * *